(12) United States Patent
Koo et al.

(10) Patent No.: US 12,416,650 B2
(45) Date of Patent: Sep. 16, 2025

(54) METHOD AND APPARATUS WITH IMPEDANCE MEASURING

(71) Applicants: SAMSUNG ELECTRONICS CO., LTD., Suwon-si (KR); Korea Advanced Institute of Science and Technology, Daejeon (KR)

(72) Inventors: Nahm il Koo, Suwon-si (KR); Minkyu Je, Daejeon (KR); Ji-Hoon Suh, Daejeon (KR); Haidam Choi, Daejeon (KR)

(73) Assignees: Samsung Electronics Co., Ltd., Suwon-si (KR); Korea Advanced Institute of Science and Technology, Daejeon (KR)

(*) Notice: Subject to any disclaimer, the term of this patent is extended or adjusted under 35 U.S.C. 154(b) by 340 days.

(21) Appl. No.: 18/188,925

(22) Filed: Mar. 23, 2023

(65) Prior Publication Data

US 2024/0118323 A1    Apr. 11, 2024

(51) Int. Cl.
*G01R 19/10*    (2006.01)
*G01R 25/00*    (2006.01)

(52) U.S. Cl.
CPC ............. *G01R 19/10* (2013.01); *G01R 25/00* (2013.01)

(58) Field of Classification Search
CPC ........ G01R 19/10; G01R 25/00; G01R 27/14; G01R 27/02; G01R 19/00; G01R 19/0053; G01R 19/165; G01R 19/16571; G01R 23/005; G01R 23/10; G01R 31/36; G01R 31/3648; G01R 31/367; A61B 5/00; A61B 5/4041; A61B 5/6833; A61B 5/7203; A61B 5/7225; A61B 5/7228; A61B 5/0531; A61B 5/053; G01N 27/02
See application file for complete search history.

(56) References Cited

U.S. PATENT DOCUMENTS

| | | |
|---|---|---|
| 6,643,540 B2 | 11/2003 | Yonce |
| 10,092,210 B2 | 10/2018 | Hwang et al. |
| 10,120,005 B2 | 11/2018 | Cherkassky et al. |
| 2020/0253500 A1 | 8/2020 | Ha et al. |

FOREIGN PATENT DOCUMENTS

KR    10-2022-0050676 A    4/2022

OTHER PUBLICATIONS

Ha et al. "A bio-impedance readout IC with digital-assisted baseline cancellation for 2-electrode measurement" *IEEE Journal of Solid-State Circuits* vol. 54 No. 11. 2019 (pp. 2969-2979).

(Continued)

*Primary Examiner* — Son T Le
(74) *Attorney, Agent, or Firm* — NSIP Law (57) ABSTRACT

An electronic device includes a baseline current generator configured to generate a baseline current based on a reference current generated by a reference current generator, variable impedance circuitry configured to receive the baseline current, and subtraction circuitry configured to receive a measured voltage based on a result of the reference current being applied to a target impedance, and an estimated voltage generated based on a result of the baseline current being applied to the variable impedance circuitry and subtract the estimated voltage from the measured voltage.

20 Claims, 9 Drawing Sheets

(56) References Cited

OTHER PUBLICATIONS

Zhang et al. "A 0.6V/0.9V 26.6-to-119.3µW ΔΣ-Based Bio-Impedance Readout IC with 101.9dB SNR and <0.1Hz 1/f Corner" *2021 IEEE International Solid-State Circuits Conference (ISSCC)*. vol. 64. IEEE, 2021 (pp. 1-3).

Park et al. "A 145.2dB-DR Baseline-Tracking Impedance Plethysmogram IC for Neckband-Based Blood Pressure and Cardiovascular Monitoring" *2022 IEEE International Solid-State Circuits Conference (ISSCC)*. vol. 65. IEEE, 2022 (pp. 1-3).

Kim et al. "Design of Sub-10-µW Sub-0.1% THD Sinusoidal Current Generator IC for Bio-Impedance Sensing" *IEEE Journal of Solid-State Circuits* vol. 57 No. 2, Feb. 2022 (pp. 586-595).

METHOD AND APPARATUS WITH IMPEDANCE MEASURING

CROSS-REFERENCE TO RELATED APPLICATIONS

This application claims the benefit under 35 USC § 119(a) of Korean Patent Application No. 10-2022-0128848, filed on Oct. 7, 2022, in the Korean Intellectual Property Office, the entire disclosure of which is incorporated herein by reference for all purposes.

BACKGROUND

1. Field

The following description relates to a method and apparatus with impedance measuring.

2. Description of Related Art

Typical approaches to measuring a bio-impedance value employ a current that is injected into a target to measure its impedance using a current generator, and a voltage signal generated by the injected current may be measured by a read-out front-end (RFE).

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In a general aspect, here is provided an electronic device including a baseline current generator configured to generate a baseline current based on a reference current generated by a reference current generator, variable impedance circuitry configured to receive the baseline current, and subtraction circuitry configured to receive a measured voltage generated by an excitation current generated based on a result of the reference current being applied to a target impedance, and an estimated voltage generated based on a result of the baseline current being applied to the variable impedance circuitry and subtract the estimated voltage from the measured voltage.

The device may include a phase extractor configured to extract a phase difference between the measured voltage and the estimated voltage based on an output voltage of the subtraction circuitry.

The variable impedance circuitry may be configured to receive the phase difference from the phase extractor, and an impedance value may be configured to be adjusted so that the phase difference becomes less than or equal to a predetermined value.

The device may include a magnitude extractor configured to extract a magnitude difference between the measured voltage and the estimated voltage based on an output voltage of the subtraction circuitry.

The baseline current generator may be configured to receive the magnitude difference from the magnitude extractor and generate the baseline current at which the magnitude difference is less than or equal to a predetermined value.

The variable impedance circuitry may include one or more resistors and one or more capacitors are mixed in series or parallel.

The baseline current includes reference current noise being generated from the reference current, the reference current noise is correlated with excitation current noise present in the excitation current.

The device may include a demodulator configured to down-convert a frequency of an output voltage of the subtraction circuitry.

In a general aspect, here is provided an electronic device including a reference current generator configured to generate a reference current, feedback circuitry configured to compensate for a magnitude difference and a phase difference of the reference current, an amplifier configured to amplify an output voltage generated that is provided to a subtraction circuit, and an analog-to-digital converter (ADC), and the feedback circuit includes a baseline current generator configured to generate a baseline current based on a current generated by the reference current generator, variable impedance circuitry configured to receive the baseline current, and the subtraction circuit. The subtraction circuit is configured to receive a measured voltage generated by an excitation current resulting from the reference current being applied to a target impedance, and an estimated voltage resulting from the baseline current being applied to the variable impedance circuitry and subtract the estimated voltage from the measured voltage.

The device may include a magnitude extractor configured to extract a magnitude difference between the measured voltage and the estimated voltage.

The baseline current generator may be configured to adjust the baseline current based on the magnitude difference where a first magnitude value of the reference current multiplied by an amplification ratio of the excitation current and a magnitude of the target impedance is equal to a second magnitude value of the reference current multiplied by an adjustment ratio of the magnitude difference and a value of the variable impedance of the variable impedance circuitry.

The variable impedance circuitry may be configured to change a phase of noise and a carrier in the baseline current to generate the estimated voltage.

In a general aspect, here is provided a method including generating a baseline current by a baseline current generator based on a reference current generated by a reference current generator, receiving, by subtraction circuitry, a measured voltage generated by an activation current resulting from the reference current being applied to a target impedance, receiving, by the subtraction circuitry, an estimated voltage resulting from the baseline current being applied to variable impedance circuitry, and subtracting, by the subtraction circuitry, the estimated voltage from the measured voltage.

The method may include extracting a phase difference between the measured voltage and the estimated voltage based on an output voltage of the subtraction circuitry.

The receiving of the estimated voltage may include receiving the phase difference by the variable impedance circuitry and adjusting an impedance value so that the phase difference becomes less than or equal to a predetermined value.

The adjusting of the impedance value may include adjusting respective connections of one or more resistors and one or more capacitors of the variable impedance circuitry.

The method may include extracting a magnitude difference between the measured voltage and the estimated voltage based on an output voltage of the subtraction circuitry.

The generating of the baseline current may include generating the baseline current, based on the baseline current generator being provided the magnitude difference, to change the magnitude difference to become less than or equal to a predetermined value.

The method may include amplifying a subtracted output from the subtraction circuitry.

The method may include down-converting, by a demodulator, an output voltage frequency of the subtraction circuitry.

In another general aspect, here is provided a non-transitory, computer-readable storage medium storing instructions that, when executed by a processor, cause the processor to perform one or more, or any combination of, the operations or methods described herein.

Other features and aspects will be apparent from the following detailed description, the drawings, and the claims.

Throughout the drawings and the detailed description, unless otherwise described or provided, the same drawing reference numerals may be understood to refer to the same or like elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences within and/or of operations described herein are merely examples, and are not limited to those set forth herein, but may be changed as will be apparent after an understanding of the disclosure of this application, except for sequences within and/or of operations necessarily occurring in a certain order. As another example, the sequences of and/or within operations may be performed in parallel, except for at least a portion of sequences of and/or within operations necessarily occurring in an order, e.g., a certain order. Also, descriptions of features that are known after an understanding of the disclosure of this application may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application. The use of the term "may" herein with respect to an example or embodiment, e.g., as to what an example or embodiment may include or implement, means that at least one example or embodiment exists where such a feature is included or implemented, while all examples are not limited thereto.

Throughout the specification, when a component or element is described as being "on", "connected to," "coupled to," or "joined to" another component, element, or layer it may be directly (e.g., in contact with the other component or element) "on", "connected to," "coupled to," or "joined to" the other component, element, or layer or there may reasonably be one or more other components, elements, layers intervening therebetween. When a component or element is described as being "directly on", "directly connected to," "directly coupled to," or "directly joined" to another component or element, there can be no other elements intervening therebetween. Likewise, expressions, for example, "between" and "immediately between" and "adjacent to" and "immediately adjacent to" may also be construed as described in the foregoing.

Although terms such as "first," "second," and "third", or A, B, (a), (b), and the like may be used herein to describe various members, components, regions, layers, or sections, these members, components, regions, layers, or sections are not to be limited by these terms. Each of these terminologies is not used to define an essence, order, or sequence of corresponding members, components, regions, layers, or sections, for example, but used merely to distinguish the corresponding members, components, regions, layers, or sections from other members, components, regions, layers, or sections. Thus, a first member, component, region, layer, or section referred to in the examples described herein may also be referred to as a second member, component, region, layer, or section without departing from the teachings of the examples.

As used herein, the term "and/or" includes any one and any combination of any two or more of the associated listed items. The phrases "at least one of A, B, and C", "at least one of A, B, or C", and the like are intended to have disjunctive meanings, and these phrases "at least one of A, B, and C", "at least one of A, B, or C', and the like also include examples where there may be one or more of each of A, B, and/or C (e.g., any combination of one or more of each of A, B, and C), unless the corresponding description and embodiment necessitates such listings (e.g., "at least one of A, B, and C") to be interpreted to have a conjunctive meaning.

The terminology used herein is for describing various examples only and is not to be used to limit the disclosure. The articles "a," "an," and "the" are intended to include the plural forms as well, unless the context clearly indicates otherwise. As non-limiting examples, terms "comprise" or "comprises," "include" or "includes," and "have" or "has" specify the presence of stated features, numbers, operations, members, elements, and/or combinations thereof, but do not preclude the presence or addition of one or more other features, numbers, operations, members, elements, and/or combinations thereof, or the alternate presence of an alternative stated features, numbers, operations, members, elements, and/or combinations thereof. Additionally, while one embodiment may set forth such terms "comprise" or "comprises," "include" or "includes," and "have" or "has" specify the presence of stated features, numbers, operations, members, elements, and/or combinations thereof, other embodiments may exist where one or more of the stated features, numbers, operations, members, elements, and/or combinations thereof are not present.

Due to manufacturing techniques and/or tolerances, variations of the shapes shown in the drawings may occur. Thus, the examples described herein are not limited to the specific shapes shown in the drawings, but include changes in shape that occur during manufacturing.

Unless otherwise defined, all terms, including technical and scientific terms, used herein have the same meaning as commonly understood by one of ordinary skill in the art to which this disclosure pertains specifically in the context on an understanding of the disclosure of the present application. Terms, such as those defined in commonly used dictionaries, are to be interpreted as having a meaning that is consistent with their meaning in the context of the relevant art and specifically in the context of the disclosure of the present application, and are not to be interpreted in an idealized or overly formal sense unless expressly so defined herein.

When measuring an impedance and a baseline component is generated in consideration of a magnitude shift and a phase shift of a reference current but a phase shift of noise is not compensated for, the noise may not be canceled perfectly. When the frequency of the voltage measured after the reference current applied to a target impedance is low, the effect is small because the phase shift due to the impedance is small, but since the phase shift increases as the frequency increases, the noise canceling effect may be reduced. Measuring a bio-impedance value by cancelling a baseline current where a reference current is applied to the target impedance may provide a dynamic range while reducing noise in a wide band in the range.

Figure 1:
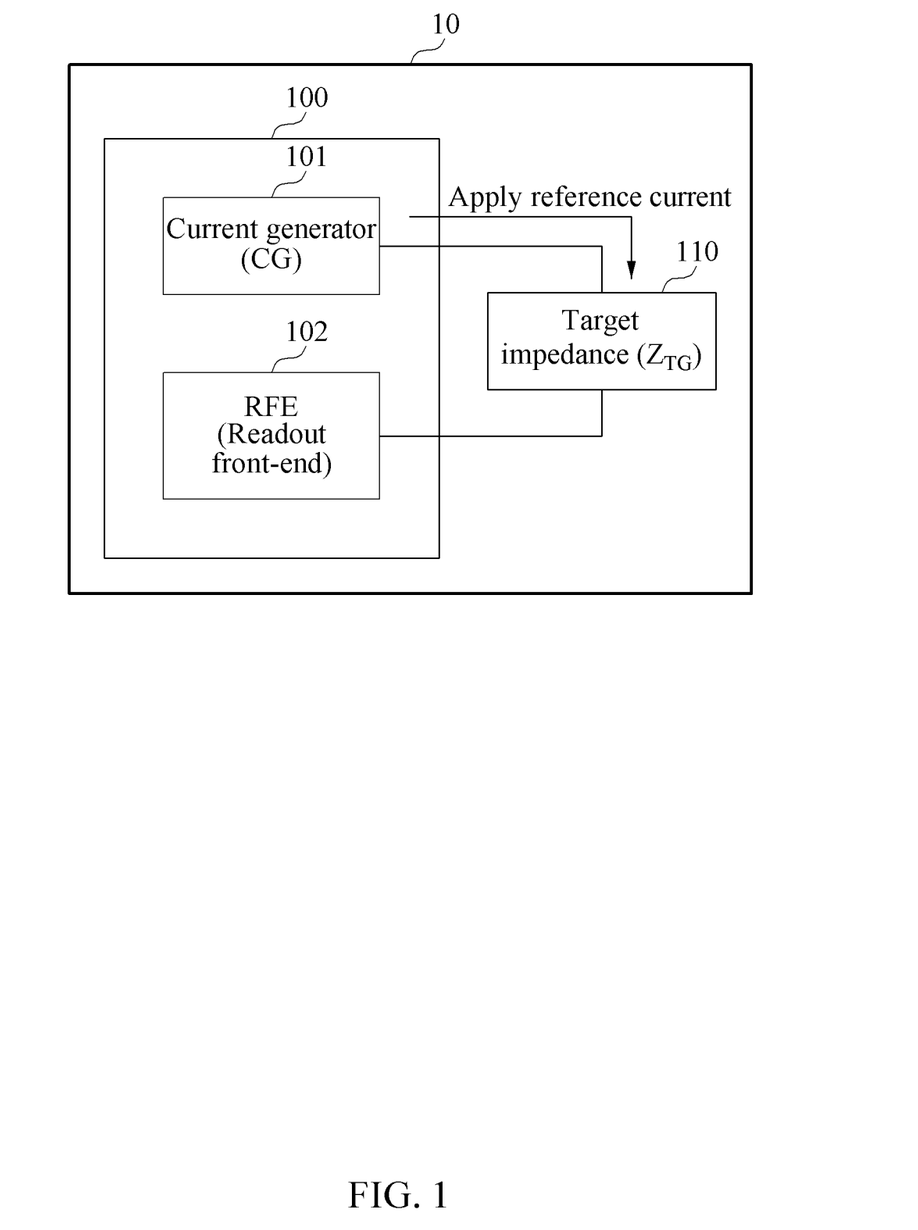
FIG. 1 illustrates an example of an electronic device with an impedance-measuring circuit according to one or more embodiments.

FIG. 1 illustrates an example of an electronic device with an impedance-measuring circuit according to one or more embodiments.

According to an example, the electronic device 10 can include an impedance-measuring circuit 100 that may include a current generator (CG) 101 and a readout front-end (RFE) 102. Herein, electronic devices, such as electronic device 10, are representative of one or more processors, or one or more processors and a memory storing instructions, configured to implement one or more, or any combination of, operations or methods described herein. The one or more processors may be respective special purpose hardware-based computers or other special-purpose hardware. The one or more processors may be configured to execute such instructions. The one or more memories may store the instructions, which when executed by the one or more processors configure the one or more processors to perform one or more, or any combination of operations of methods described herein.

In an example, an object may have its impedance measured as a target impedance (ZTG) 110. In some examples, the object being measured for its impedance may be an animal's nerve. For example, when the impedance-measuring circuit 100 is used to check whether a neural signal generated is generated in peripheral nerves at a specific location. When the impedance-measuring circuit 100 is used in a system (e.g., a health patch, a smartwatch, etc.) for monitoring a user's condition, such as a state of the user's health, the object being measured may be a human, and the impedance-measuring circuit 100 may be applied to a wearable sensor to measure an impedance of a part of the human body.

In a non-limiting example, the impedance-measuring circuit 100, the CG 101 may generate a reference current and apply it to the target impedance 110. The impedance-measuring circuit 100 may extract the target impedance 110 by applying the reference current to the target impedance 110 and measuring a resulting voltage that is generated by the RFE 102.

In an example, the RFE 102 may generate a baseline component for noise canceling, and the RFE 102 may process a subtle variation in the impedance of the object by removing the baseline component from the voltage generated in the target impedance 110.

In a non-limiting example, the target impedance may be modeled as a complex structure having both resistances and reactance components. Because of the reactance components, when the reference current passes through the target impedance and is converted into a voltage signal, the magnitude and the phase may change. Accordingly, when the baseline component is generated, the RFE 102 may consider a magnitude shift and a phase shift.

In an example, the reference current generated by the current generator 101 may include noise. Accordingly, when the reference current passes through the target impedance and is converted into the voltage signal, the magnitude shift and the phase shift of the noise may also occur.

In a non-limiting example, the impedance measuring circuit 100 may perform noise canceling by compensating for the phase shift of the noise and a carrier signal corresponding to the baseline using a variable impedance.

Figure 2A:
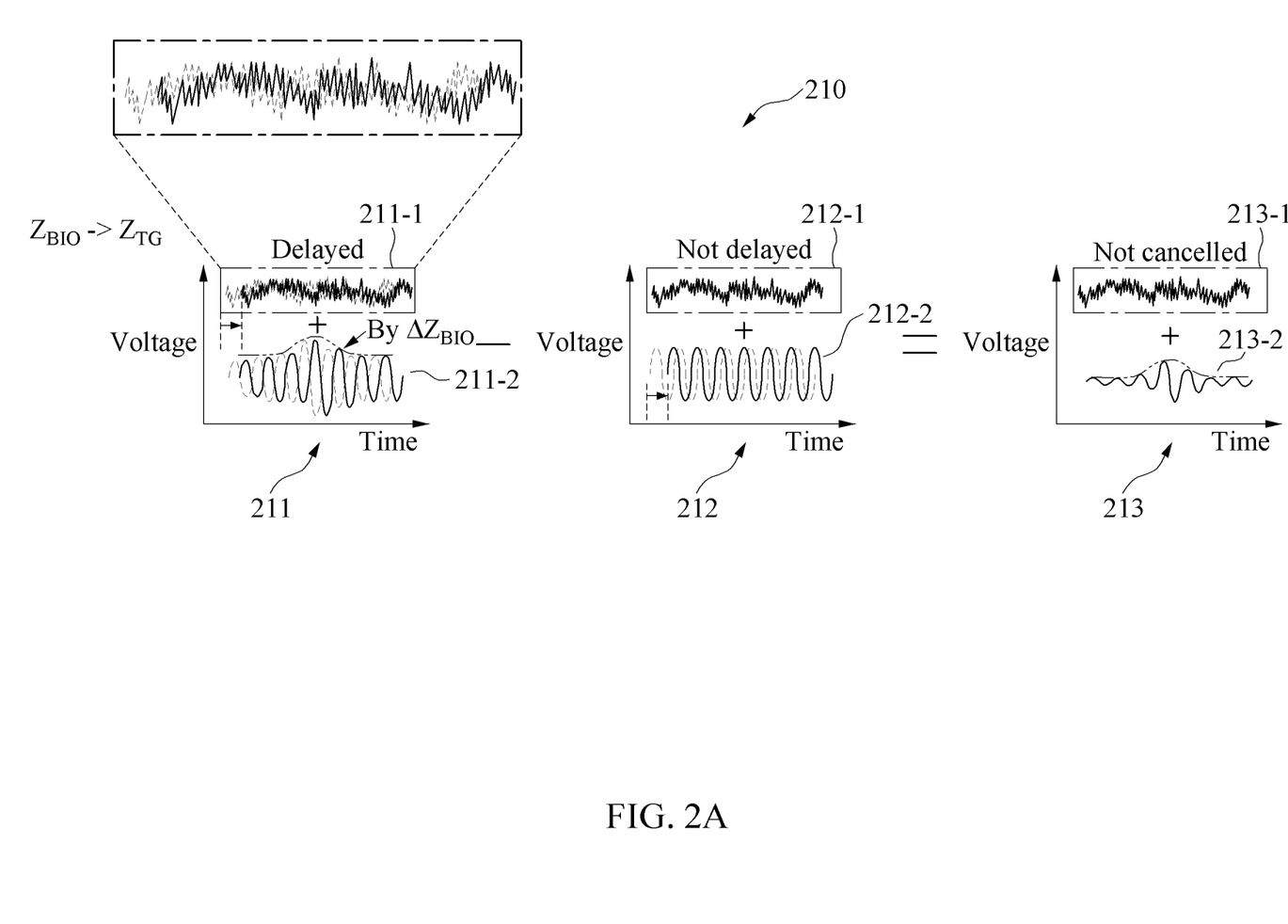
FIG. 2A illustrates an example of noise canceling of an impedance-measuring circuit according to one or more embodiments.

FIG. 2A illustrates an example of a noise canceling process of an impedance-measuring circuit according to one or more embodiments.

The description provided with reference to FIG. 1 may be applicable to the example of FIG. 2A, and thus redundant descriptions thereof will be omitted.

Examples of noise-canceling processes 210 may be performed by the impedance-measuring circuit 100 of FIG. 1.

In a first example, graph 211 illustrates a measured voltage after a reference current passes through a target impedance by dividing it into a carrier and a noise. In graph 211, two waveforms are visible in noise 211-1, there being a dotted line of noise waveform 211-1 which may be noise of an existing reference current and a solid line waveform which may be noise of an excitation current. In graph 211, there are also two lines visible in carrier waveform 211-2, where a dotted line of the carrier waveform 211-2 may be a waveform of a carrier of an existing reference current and a solid line waveform may be a carrier waveform after passing through, or being applied to, the target impedance 110. Referring to graph 211, a delay may occur as the noise waveforms 211-1 and the carrier waveforms 211-2 pass through the target impedance 110.

In a second example, graph 212 represents a voltage of a baseline current over time. In graph 212, a solid line of a baseline noise waveform 212-1 may be noise of the baseline current. In graph 212, there may be two waveforms visible in the baseline carrier waveform 212-2, including a dotted line waveform of the baseline carrier waveform 212-2 which may be a carrier waveform of an existing baseline current and a solid line waveform which may be a carrier waveform in which an input delay is reflected in the baseline current.

Referring to graph 212, a delay may not occur in the baseline noise waveforms 212-1 but a delay may occur in the baseline carrier waveforms 212-2.

In a third example, graph 213 represents a voltage over time after performing noise canceling. Referring to graph 213, in an output noise 213-1, it may be confirmed that the noise waveform 211-1 is not canceled and residual components exist. In an output carrier 213-2, it may be confirmed that the carrier waveform 211-2 is canceled by the baseline carrier waveform 212-2 and only a variation by the target impedance 110 exists. The carrier waveform 211-2 may be canceled by adjusting the size of the baseline carrier waveform 212-2 through an input delay (e.g., a delay may be possible by controlling the start point of a signal) but since the delay is not reflected on the baseline noise waveform 212-1, the noise waveform 211-1 may not be canceled.

Figure 2B:
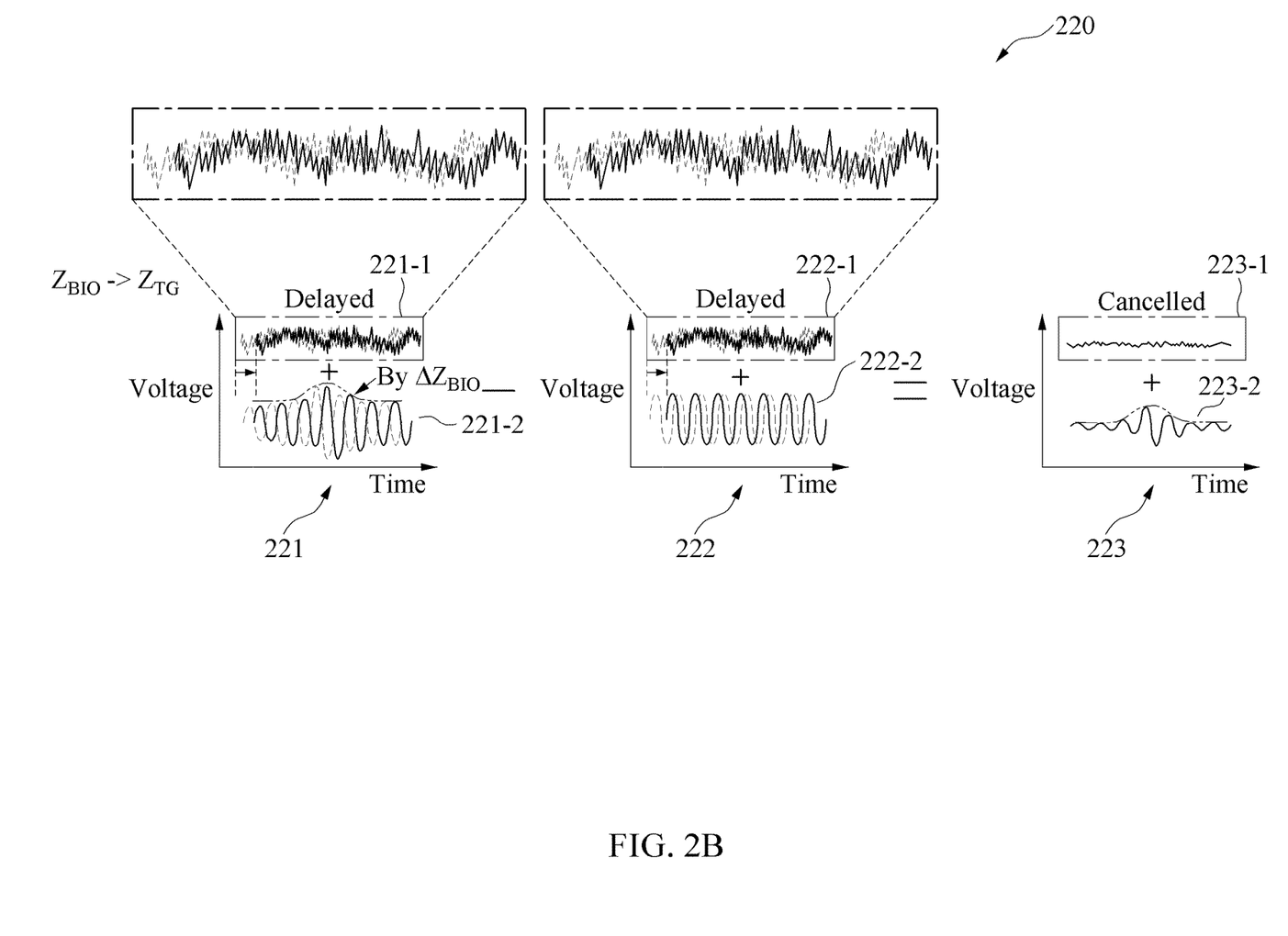
FIG. 2B illustrates an example of noise canceling as a voltage graph in an impedance-measuring circuit to which a noise delay is applied according to one or more embodiments.

FIG. 2B illustrates an example of noise canceling as a voltage graph in an impedance-measuring circuit to which a noise delay is applied according to one or more embodiments.

The description with reference to FIG. 2A may be applied to the description with reference to FIG. 2B, and thus a duplicated description will be omitted.

Noise-canceling 220 according to an example may be performed by an impedance-measuring device described in further detail below with reference to FIGS. 3 to 7B.

Referring to FIG. 2B, graph 221 according to an example represents a voltage over time of an activation current and may be generated through the same process as graph 211 of FIG. 2A.

In a non-limiting example, graph 222 may represent a voltage of a baseline current over time. In order to apply a delay to a carrier included in the baseline current, an inherent noise, and a harmonic, a phase shift may be made overall inside the circuit. Two waveforms are present in graph 222, where dotted line is of a baseline noise waveform 222-1, which may be noise of an existing baseline current waveform, and a waveform illustrated by a solid line may be noise of the baseline current in which a phase shift delay is reflected. In graph 222, a dotted line of a baseline carrier 222-2 waveform may be a carrier waveform of an existing baseline current and a solid line may be a carrier waveform in which an input delay or the phase shift delay is reflected in the baseline current.

In an example, graph 223 represents a voltage over time after performing noise canceling. Referring to graph 223, in an output noise waveform 223-1, noise waveform 221-1 may be substantially canceled by the baseline noise waveform 222-1. In an output carrier waveform 223-2, it may be confirmed that a carrier waveform 221-2 is canceled by the baseline carrier waveform 222-2, and only a variation by the target impedance exists.

Figure 3:
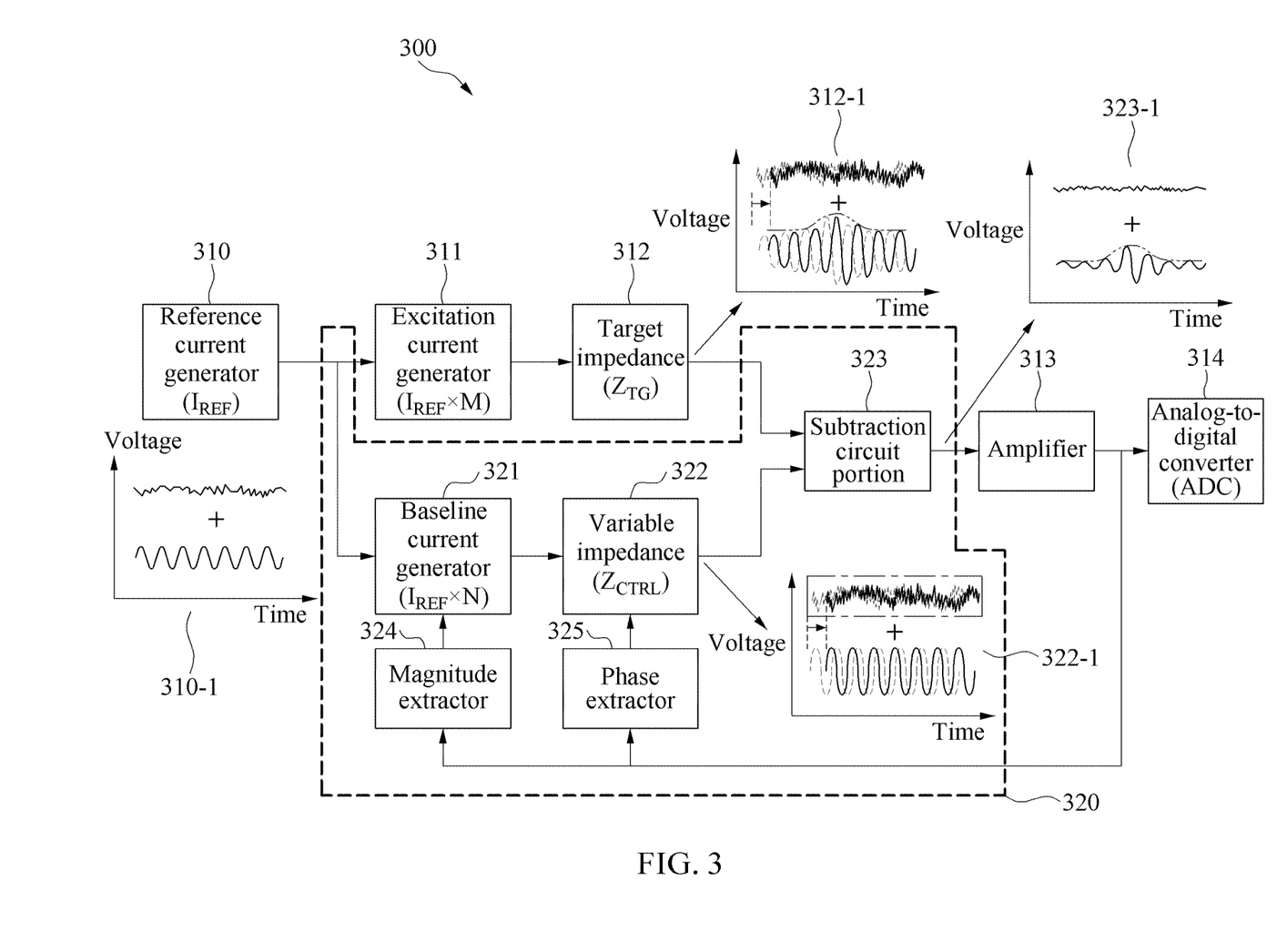
FIG. 3 illustrates an example of an impedance-measuring circuit having feedback according to one or more embodiments.

FIG. 3 illustrates an example of an impedance-measuring circuit having feedback according to one or more embodiments.

As illustrated in FIG. 3, one or more blocks and a combination thereof may be implemented by an electronic device, for example.

The description with reference to FIG. 2B may be applied to FIG. 3, and thus a duplicated description will be omitted.

An impedance-measuring circuit 300, according to an example, may include a reference current generator 310, an excitation current generator 311, an amplifier 313, an ADC 314, and feedback circuitry 320. However, the components of the impedance-measuring circuit 300 of the example are not limited to the described example.

The feedback circuitry 320, according to an example, may include a baseline current generator 321, variable impedance circuitry ($Z_{CTRL}$) 322, a subtraction circuitry 323, a magnitude extractor 324, and a phase extractor 325. However, the components of the feedback circuitry 320 of the example are not limited to the described example.

A target impedance (ZTG) 312, according to an example, may be the same as the target impedance 110 describe above in FIG. 1.

A detailed operation of the impedance-measuring device 300 of FIG. 3 which will be described in further detail below with reference to FIG. 4.

Figure 4:
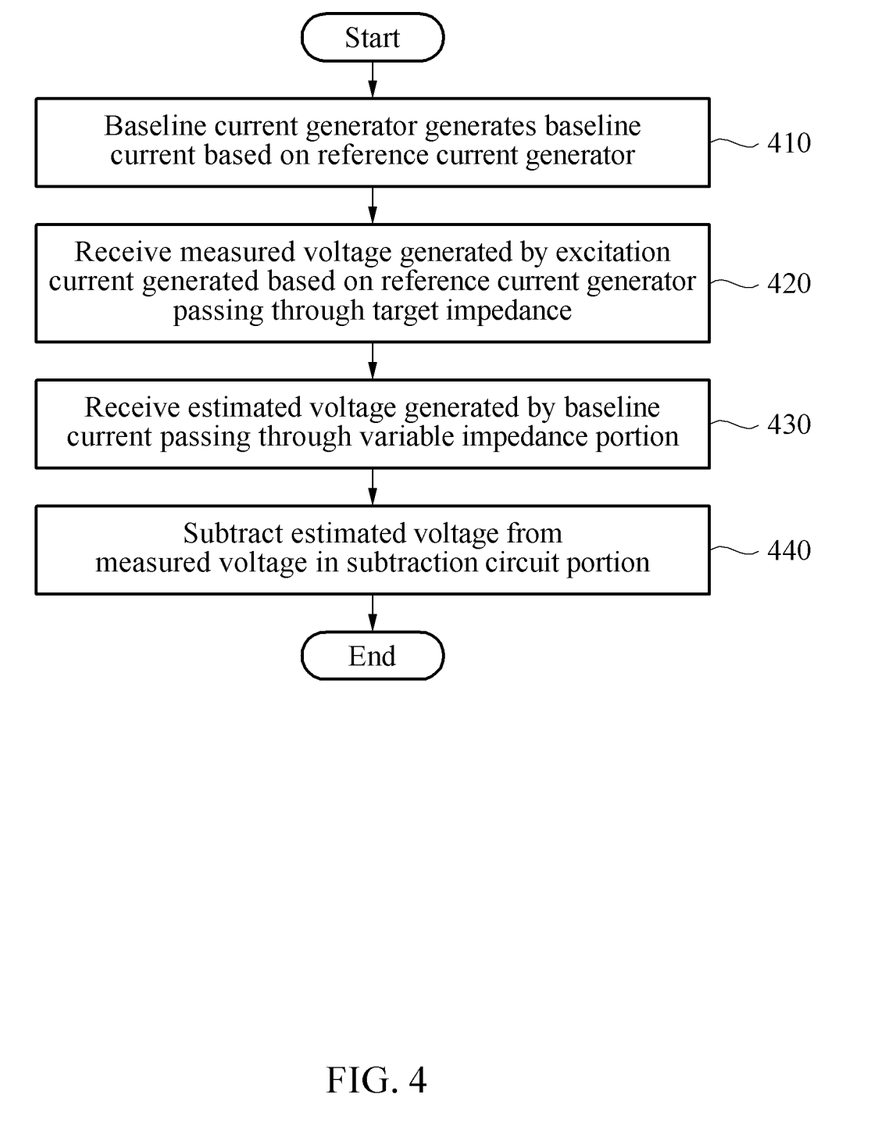
FIG. 4 illustrates an example of a method of controlling an impedance-measuring device according to one or more embodiments.

FIG. 4 illustrates an example of a method of controlling an impedance-measuring device according to one or more embodiments.

The description with reference to FIG. 3 may be applied to FIG. 4 and thus a duplicated description will be omitted.

Operations of FIG. 4 may be performed in the shown order and manner. However, the order of some operations may change, or some of the operations may be omitted, without departing from the spirit and scope of the shown example. The operations shown in FIG. 4 may be performed in parallel or simultaneously. The operations shown in FIG. 4 may be implemented by an electronic device.

The reference current generator 310, according to an example, may generate a reference current and a voltage (e.g., graph 310-1) having noise and a carrier. The reference current may be transmitted to the activation current generator 311 and the baseline current generator 321.

In operation 410, in the impedance-measuring device 300 according to an example, the baseline current generator 321 may generate a baseline current based on the reference current generated by the reference current generator 310.

The baseline current generator 321, according to an example, may receive a reference current and generate a baseline current based on the reference current. The baseline current generator 321, according to an example, may include a magnitude controller that may amplify a current. The baseline current may be a current generated by amplifying a reference current value. The baseline current may be transmitted to the variable impedance circuitry 322. A detailed description of the magnitude controller will be described in further detail below with reference to FIG. 5.

In operation 420, in the impedance-measuring device 300 according to an example, the subtraction circuitry 323 may receive a measured voltage generated by an excitation current generated based on the reference current being applied to the target impedance 312.

In an example, the excitation current generator 311 may receive the reference current and generate the excitation current based on the reference current. The activation current may be a current generated by amplifying a reference current value. The excitation current may be applied to the target impedance 312. The measured voltage (e.g., graph 312-1) generated by the excitation current being applied to the target impedance 312 may be transmitted to the subtraction circuitry 323.

In operation 430, in the impedance-measuring device 300 according to an example, the subtraction circuitry may receive an estimated voltage generated by the baseline current being applied to the variable impedance circuitry.

In a non-limiting example, the variable impedance circuitry 322 may include a phase controller that may change a phase of a current. The variable impedance circuitry 322, according to an example, may receive a baseline current and change the phase of noise and a carrier included in the baseline current (e.g., the noise 222-1 and the carrier 222-2 of FIG. 2B). The estimated voltage (e.g., graph 322-1) generated by the baseline current being applied to the variable impedance circuitry 322 may be transmitted to the subtraction circuitry 323. A detailed description of the phase controller will be described in further detail below with reference to FIG. 5.

In operation 440, in the impedance-measuring device 300 according to an example, the subtraction circuitry may subtract the estimated voltage from the measured voltage.

The subtraction circuitry 323, according to an example, may receive the measured voltage and the estimated voltage and may subtract the estimated voltage from the measured voltage. By subtracting the estimated voltage from the measured voltage, an output voltage (e.g., graph 323-1) may be extracted. By using the output voltage, the target impedance 312 may be extracted. The subtraction circuitry 323 may transmit the output voltage (e.g., graph 323-1) to the amplifier 313.

In an example, the amplifier 313 may amplify the magnitude of the received output voltage. The amplifier 313 may transmit the amplified output voltage to the magnitude extractor 324 and the phase extractor 325. Because the amplified output voltage differs only in magnitude from the output voltage of the subtraction circuitry 323, the amplified output voltage may be generated based on the output voltage of the subtraction circuitry 323. Accordingly, the magnitude extractor 324 and the phase extractor 325 may perform a series of operations based on the output voltage of the subtraction circuitry 323.

The magnitude extractor 324, according to an example, may extract a magnitude difference between the measured voltage and the estimated voltage based on the output voltage received from the amplifier. The magnitude extractor 324 will be described in further detail below with reference to FIG. 5.

In an example, the phase extractor 325 may extract a phase difference between the measured voltage and the estimated voltage based on the output voltage received from the amplifier. The phase extractor 325 will be described in further detail below with reference to FIG. 5.

The ADC 314, according to an example, may convert the amplified output voltage into digital units or values and extract the target impedance 312 using the output voltage converted into the digital units or values.

Figure 5:
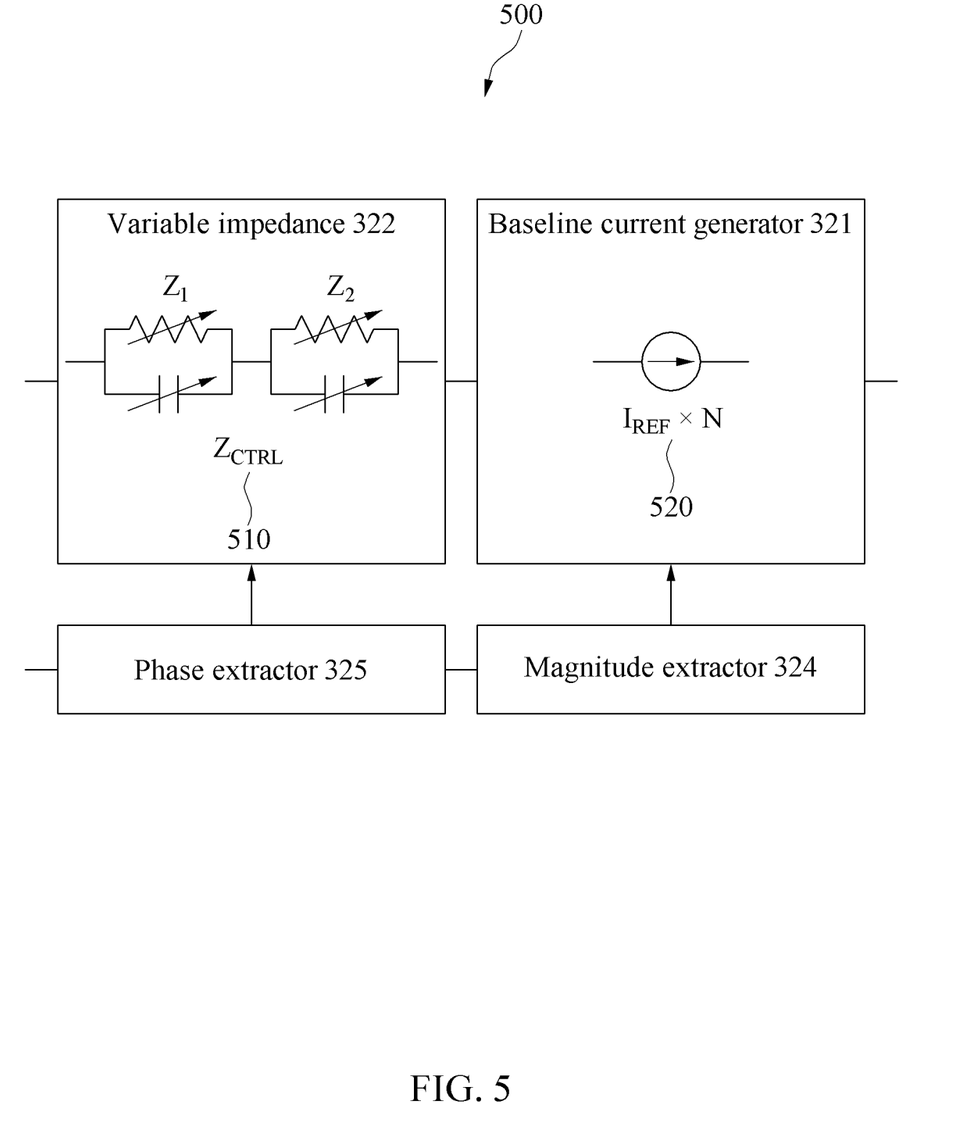
FIG. 5 illustrates an example of a phase controller and a magnitude controller according to one or more embodiments.

FIG. 5 illustrates an example of a phase controller and a magnitude controller according to one or more embodiments.

The description provided with reference to FIGS. 2B to 4 may be applied to the description of FIG. 5, and thus a duplicate description will be omitted.

In a non-limiting example, a phase controller 510 may be included in the variable impedance circuitry 322 of FIG. 3.

The target impedance 312, according to an example, may have a structure in which at least one resistor and at least one reactance are complexly mixed in series or in parallel. When the target impedance 312 includes a complex combination of resistor and reactance, a phase shift of the activation current may occur by the reactance component of the target impedance 312.

The phase controller 510, according to an example, may include a circuit connecting one or more variable resistors (e.g., resistor banks) and one or more variable capacitors (e.g., capacitor banks) in series or in parallel.

The phase extractor 325, according to an example, may extract a phase difference between the measured voltage and the estimated voltage based on the output voltage received from the amplifier. The phase controller 510, according to an example, may receive a phase difference from the phase extractor 325 and an impedance value may be adjusted so that the phase difference may be less than or equal to a predetermined value.

According to an example, the variable resistor and the variable capacitor may be connected in parallel and constitute one variable impedance, and may include a circuit in which at least one variable impedance is connected in series with each other. The phase controller 510 including a combination of the variable resistor and the variable capacitor may change the phase of the baseline current in response to the phase of the excitation current changed by the target impedance 312 based on the phase difference received by the phase extractor 325. The variable impedance circuitry of the example illustrates an example in which a structure having the variable resistor and the variable capacitor are connected in parallel and constitute one variable impedance, and two variable impedances are connected in series with each other but are not limited to the described example.

For example, when the phase difference received from the phase extractor 325 is 30° and the predetermined value is 1°, the variable impedance circuitry 322 may adjust the impedance value so that the phase shift may be generated 29° greater than or less than the previous shift.

In a non-limiting example, magnitude controller 520 may be included in the baseline current generator 321 of FIG. 3. The magnitude extractor 324, according to an example, may extract a magnitude difference between the measured voltage and the estimated voltage based on the output voltage received from the amplifier. The baseline current generator 321, according to an example, may receive the magnitude difference from the magnitude extractor 324 and may generate a baseline current in which the magnitude difference may be less than or equal to a predetermined value using the magnitude controller 520.

Referring to Equation 1 below, the magnitude controller 520, in an example, may adjust the baseline current so that the magnitude of the value in which the reference current IREF value multiplied by the amplification ratio M of the excitation current generator 311 and the magnitude of the target impedance is equal to the magnitude of the value in which the reference current IREF value multiplied by adjustment ratio N reflecting the magnitude difference determined by the magnitude extractor 324 and the variable impedance circuitry $Z_{CTRL}$.

$$I_{REF} \times M \times Z_{TG} = I_{REF} \times N \times Z_{CTRL} \quad \text{Equation 1}$$

For example, when the magnitude difference received from the magnitude extractor 324 is 3 nanovolt (nV) and the predetermined value is 0.1 nV, the baseline current generator 321 may generate a baseline current so that the voltage magnitude may be greater than or less than the previous magnitude by 2.9 nV.

Figure 6:
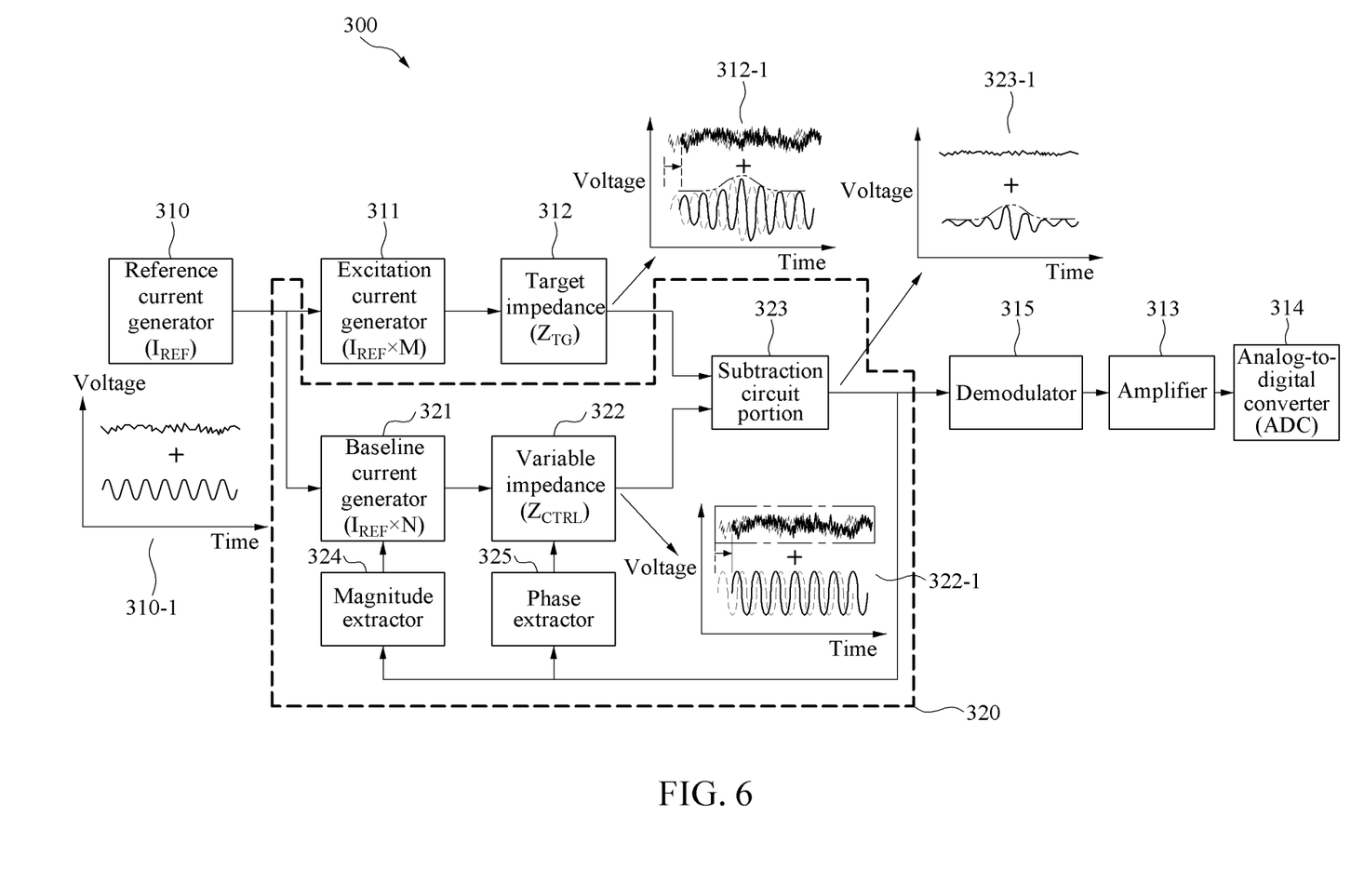
FIG. 6 illustrates an example of an impedance-measuring circuit including a demodulator according to one or more embodiments.

FIG. 6 illustrates an example of an impedance-measuring circuit including a demodulator according to one or more examples.

The description with reference to FIGS. 2B to 5 may be applied to the example of FIG. 6 and blocks having the same reference number may perform the same function. A duplicate description will be omitted. In FIG. 6, one or more blocks and a combination thereof may be implemented by a special-purpose hardware-based computer that performs a predetermined function, or a combination of computer instructions and special-purpose hardware.

Referring to FIG. 6, the demodulator 315, according to an example, may be positioned between the subtraction circuitry 323 and the amplifier 313. The demodulator 315 may down-convert the frequency of an output voltage of the subtraction circuitry 323. When down-conversion is performed, a bandwidth required by the amplifier 313 may be mitigated and a sampling frequency of the ADC 314 may be further lowered, and efficient conversion may be possible.

Figure 7A:
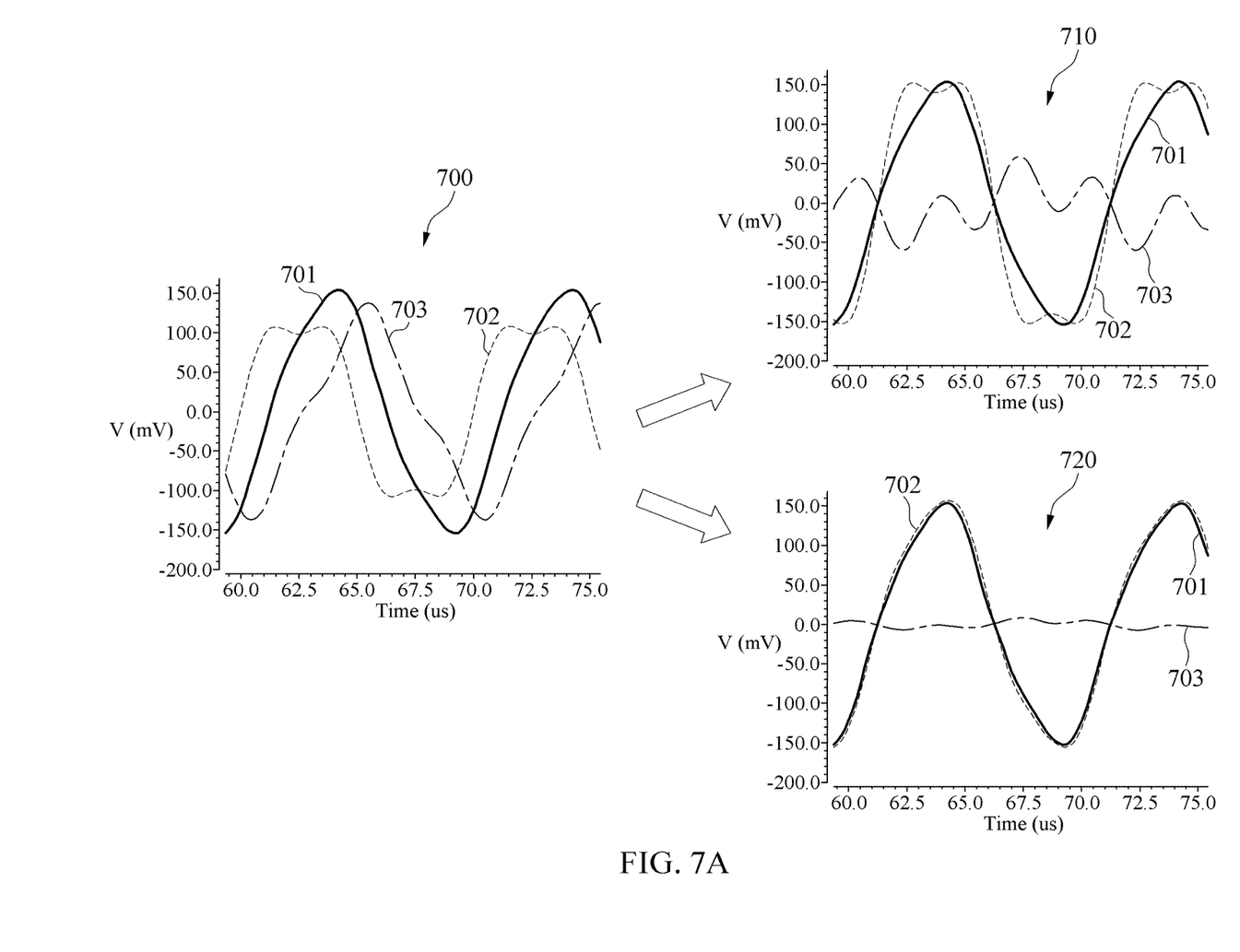
FIGS. 7A and 7B illustrate an example of a simulation result according to one or more embodiments.
Figure 7B:
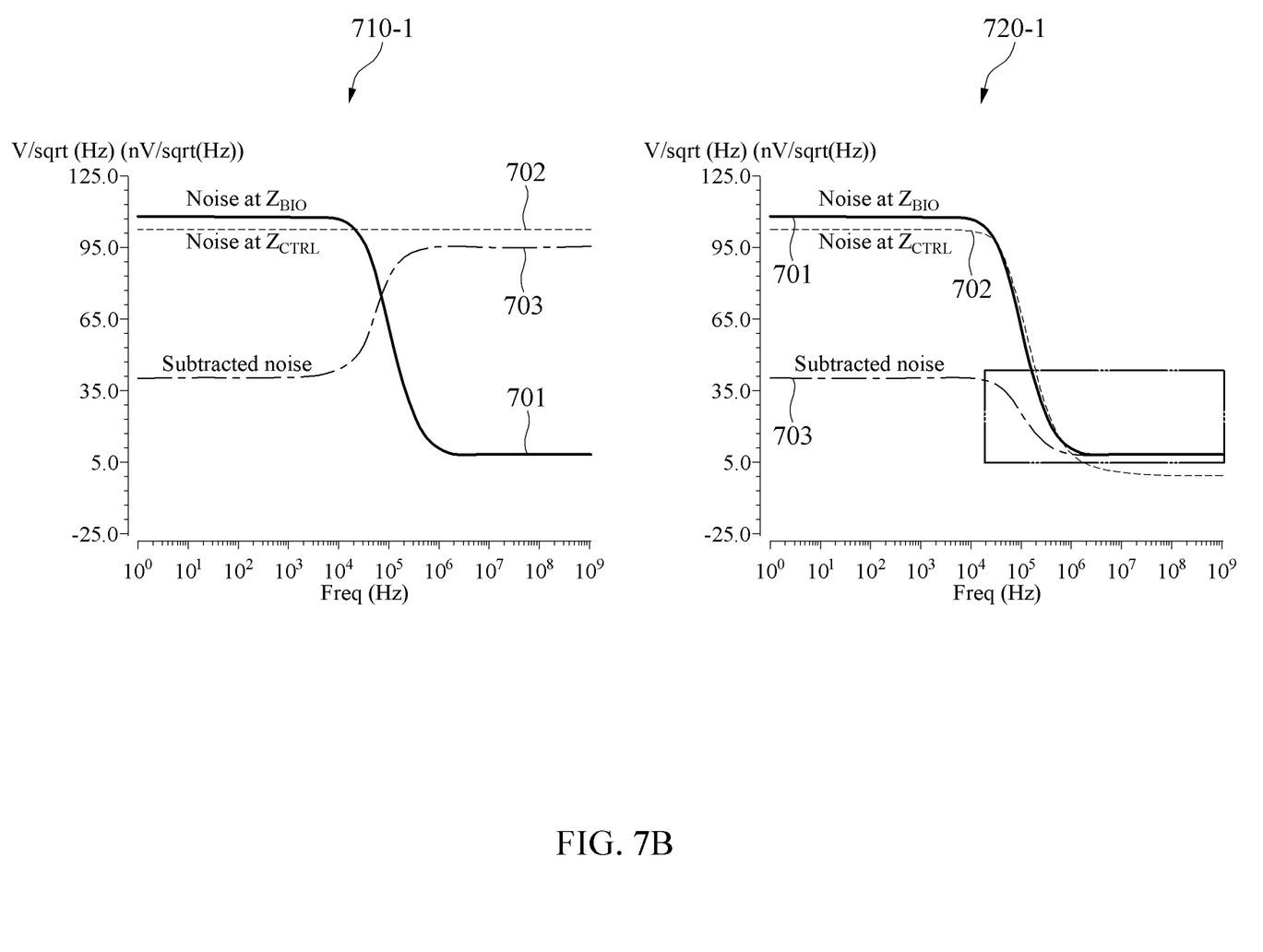

FIGS. 7A and 7B illustrate an example of a simulation result according to one or more examples.

The description provided with reference to FIGS. 1 to 5 may be applied to the description of FIGS. 7A and 7B, and thus a duplicate description will be omitted.

Graphs 700 to 720-1 are all simulated from the current of the same reference current generator 310.

Graph 700 illustrates an example where a delay is not applied to a carrier and noise of a baseline current generated by the baseline current generator 321 of the impedance-measuring circuit 300, a measured voltage 701, an estimated voltage 702, and an output voltage 703.

Referring to the output voltage 703, according to an example, since the baseline current carrier and noise are not canceled, the target impedance 312 may not be extracted from the output voltage 703.

Graph 710 illustrates in which an input delay is applied to the carrier in the baseline current generator 321 in the impedance-measuring circuit 300 according to an example, the measured voltage 701, the estimated voltage 702, and the output voltage 703.

Referring to the output voltage 703, according to an example, the carrier is canceled, but the noise is not canceled, and thus the output voltage 703 may be extracted in a form in which the noise is included in the target impedance 312.

Graph 720 illustrates an example where the baseline current generated by the baseline current generator 321 passes through the variable impedance circuitry 322 and a phase shift is applied in the impedance-measuring circuit 300 according to an example, the measured voltage 701, the estimated voltage 702, and the output voltage 703.

Referring to the output voltage 703, according to an example, the carrier and the noise are canceled and the target impedance 312 may be extracted from the output voltage 703.

Graph 710-1, according to an example, illustrates a voltage value of the noise of the measured voltage 701, the estimated voltage 702, and the output voltage 703 of graph 710 according to the frequency shift.

Graph 720-1, according to an example, illustrates a voltage value of the noise of the measured voltage 701, the estimated voltage 702, and the output voltage 703 of graph 720 according to the frequency shift.

The electronic devices, processors, memories, impedance-measuring circuit 100, readout front-end (RFE) 102, current generator (CG) 101, phase extractor 325, magnitude distractor 324, variable impedance 322, and baseline current generator 324 described herein and disclosed herein described with respect to FIGS. 1-7B are implemented by or representative of hardware components. As described above, or in addition to the descriptions above, examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. As described above, or in addition to the descriptions above, example hardware components may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-7B that perform the operations described in this application may be performed by circuitry or controller computing hardware, for example, by one or more processors or computers, implemented as described above implementing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions herein, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media, and thus, not a signal per se. As described above, or in addition to the descriptions above, examples of a non-transitory computer-readable storage medium include one or more of any of read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and/or any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents.

Therefore, in addition to the above and all drawing disclosures, the scope of the disclosure is also inclusive of the claims and their equivalents, i.e., all variations within the scope of the claims and their equivalents are to be construed as being included in the disclosure.

What is claimed is:

1. An electronic device, the device comprising:
   a baseline current generator configured to generate a baseline current based on a reference current generated by a reference current generator;
   variable impedance circuitry configured to receive the baseline current; and
   subtraction circuitry configured to:
      receive a measured voltage generated by an excitation current generated based on a result of the reference current being applied to a target impedance, and an estimated voltage generated based on a result of the baseline current being applied to the variable impedance circuitry; and
      subtract the estimated voltage from the measured voltage.

2. The device of claim 1, further comprising:
   a phase extractor configured to extract a phase difference between the measured voltage and the estimated voltage based on an output voltage of the subtraction circuitry.

3. The device of claim 2, wherein the variable impedance circuitry is configured to receive the phase difference from the phase extractor, and
   wherein an impedance value is configured to be adjusted so that the phase difference becomes less than or equal to a predetermined value.

4. The device of claim 1, further comprising:
   a magnitude extractor configured to extract a magnitude difference between the measured voltage and the estimated voltage based on an output voltage of the subtraction circuitry.

5. The device of claim 4, wherein the baseline current generator is configured to:
   receive the magnitude difference from the magnitude extractor; and
   generate the baseline current at which the magnitude difference is less than or equal to a predetermined value.

6. The device of claim 1, wherein the variable impedance circuitry comprises one or more resistors and one or more capacitors are mixed in series or parallel.

7. The device of claim 1, wherein the baseline current comprises reference current noise being generated from the reference current, and
   wherein the reference current noise is correlated with excitation current noise present in the excitation current.

8. The device of claim 1, further comprising:
   a demodulator configured to down-convert a frequency of an output voltage of the subtraction circuitry.

9. An electronic device, the device comprising:
   a reference current generator configured to generate a reference current;
   feedback circuitry configured to compensate for a magnitude difference and a phase difference of the reference current;
   an amplifier configured to amplify an output voltage generated that is provided to a subtraction circuit; and
   an analog-to-digital converter (ADC),
   wherein the feedback circuit comprises:
      a baseline current generator configured to generate a baseline current based on a current generated by the reference current generator;

variable impedance circuitry configured to receive the baseline current; and the subtraction circuit, wherein the subtraction circuit is configured to:
receive a measured voltage generated by an excitation current resulting from the reference current being applied to a target impedance, and an estimated voltage resulting from the baseline current being applied to the variable impedance circuitry; and
subtract the estimated voltage from the measured voltage.

10. The device of claim 9, further comprising a magnitude extractor configured to extract a magnitude difference between the measured voltage and the estimated voltage.

11. The device of claim 10, wherein the baseline current generator is further configured to adjust the baseline current based on the magnitude difference where a first magnitude value of the reference current multiplied by an amplification ratio of the excitation current and a magnitude of the target impedance is equal to a second magnitude value of the reference current multiplied by an adjustment ratio of the magnitude difference and a value of the variable impedance of the variable impedance circuitry.

12. The device of claim 9, wherein the variable impedance circuitry is configured to change a phase of noise and a carrier in the baseline current to generate the estimated voltage.

13. A method, the method comprising:
generating a baseline current by a baseline current generator based on a reference current generated by a reference current generator;
receiving, by subtraction circuitry, a measured voltage generated by an activation current resulting from the reference current being applied to a target impedance;
receiving, by the subtraction circuitry, an estimated voltage resulting from the baseline current being applied to variable impedance circuitry; and
subtracting, by the subtraction circuitry, the estimated voltage from the measured voltage.

14. The method of claim 13, further comprising:
extracting a phase difference between the measured voltage and the estimated voltage based on an output voltage of the subtraction circuitry.

15. The method of claim 14, wherein the receiving of the estimated voltage comprises receiving the phase difference by the variable impedance circuitry and adjusting an impedance value so that the phase difference becomes less than or equal to a predetermined value.

16. The method of claim 15, wherein the adjusting of the impedance value comprises adjusting respective connections of one or more resistors and one or more capacitors of the variable impedance circuitry.

17. The method of claim 13, further comprising:
extracting a magnitude difference between the measured voltage and the estimated voltage based on an output voltage of the subtraction circuitry.

18. The method of claim 17, wherein the generating of the baseline current comprises generating the baseline current, based on the baseline current generator being provided the magnitude difference, to change the magnitude difference to become less than or equal to a predetermined value.

19. The method of claim 13, further comprising:
amplifying a subtracted output from the subtraction circuitry.

20. The method of claim 13, further comprising:
down-converting, by a demodulator, an output voltage frequency of the subtraction circuitry.

* * * * *

UNITED STATES PATENT AND TRADEMARK OFFICE
CERTIFICATE OF CORRECTION

| | | |
|---|---|---|
| PATENT NO. | : 12,416,650 B2 | Page 1 of 1 |
| APPLICATION NO. | : 18/188925 | |
| DATED | : September 16, 2025 | |
| INVENTOR(S) | : Nahm il Koo et al. | |

It is certified that error appears in the above-identified patent and that said Letters Patent is hereby corrected as shown below:

On the Title Page

Item (30) Please insert as follows:
--Foreign Application Priority Data
Oct. 7, 2022 (KR) --------- 10-2022-0128848--

Signed and Sealed this
Twenty-first Day of October, 2025

John A. Squires
*Director of the United States Patent and Trademark Office*